United States Patent
Miceli et al.

(10) Patent No.: US 9,427,377 B1
(45) Date of Patent: Aug. 30, 2016

(54) COMPLIANCE PILL TRAY SYSTEM

(71) Applicant: Tri State Distribution, Inc., Sparta, TN (US)

(72) Inventors: David A. Miceli, Reno, NV (US); Joseph A. Miceli, Spencer, TN (US)

(73) Assignee: Tri State Distribution, Inc., Sparta, TN (US)

( * ) Notice: Subject to any disclaimer, the term of this patent is extended or adjusted under 35 U.S.C. 154(b) by 139 days.

(21) Appl. No.: 14/323,253

(22) Filed: Jul. 3, 2014

Related U.S. Application Data

(63) Continuation-in-part of application No. 14/304,204, filed on Jun. 13, 2014, which is a continuation-in-part of application No. 13/746,671, filed on Jan. 22, 2013, now abandoned.

(51) Int. Cl.
*A61J 7/04* (2006.01)
*G08B 21/24* (2006.01)
*G06F 19/00* (2011.01)

(52) U.S. Cl.
CPC .............. *A61J 7/04* (2013.01); *G06F 19/3462* (2013.01); *G08B 21/24* (2013.01); *A61J 2200/30* (2013.01)

(58) Field of Classification Search
CPC ...... A61J 7/04; A61J 7/0436; A61J 2200/30; A61J 7/0418–7/0481; G06F 19/3456–19/3475; G08B 21/24
See application file for complete search history.

(56) References Cited

U.S. PATENT DOCUMENTS

| | | | |
|---|---|---|---|
| 4,749,085 A | 6/1988 | Denney | |
| 5,014,798 A | 5/1991 | Glynn | |
| 5,159,581 A | 10/1992 | Agans | |
| 5,408,443 A * | 4/1995 | Weinberger | A61J 7/0481 221/3 |
| 5,826,217 A | 10/1998 | Lerner | |
| 6,294,999 B1 * | 9/2001 | Yarin | A61J 7/0481 340/573.1 |
| 6,375,956 B1 * | 4/2002 | Hermelin | A61J 7/04 206/528 |
| 6,380,858 B1 * | 4/2002 | Yarin | A61J 7/0481 128/903 |
| 6,464,506 B1 * | 10/2002 | Welles | A61G 12/00 206/459.5 |
| 6,550,618 B2 | 4/2003 | Peterson | |
| 6,574,165 B2 | 6/2003 | Sharma et al. | |
| 7,907,477 B2 | 3/2011 | Puzia | |
| 7,926,850 B1 * | 4/2011 | Muncy | A61J 7/0084 206/570 |
| 8,174,370 B1 | 5/2012 | Fulmer-Mason | |
| 8,193,918 B1 * | 6/2012 | Shavelsky | A61J 7/04 340/309.16 |
| 8,583,281 B2 | 11/2013 | Bear et al. | |
| 8,799,016 B1 | 8/2014 | Cohan | |
| 2002/0027507 A1 * | 3/2002 | Yarin | A61J 7/0481 340/573.1 |
| 2002/0067270 A1 * | 6/2002 | Yarin | A61J 7/0481 340/573.1 |
| 2004/0133305 A1 * | 7/2004 | Jean-Pierre | G06F 19/3462 700/231 |
| 2004/0188998 A1 | 9/2004 | Henthorn | |
| 2004/0243445 A1 | 12/2004 | Keene | |
| 2005/0109658 A1 | 5/2005 | Bindford | |

(Continued)

*Primary Examiner* — Hai Phan
*Assistant Examiner* — Orlando Bousono
(74) *Attorney, Agent, or Firm* — Luedeka Neely Group, P.C.

(57) ABSTRACT

Compliance calendars distributed in connection with prescription containers configured to improve compliance by a patient in taking a prescription medication, the compliance calendars configured to include a frequency reminder and one or more sequence reminders of the times to take the medicine during each frequency.

34 Claims, 9 Drawing Sheets

(56) References Cited

U.S. PATENT DOCUMENTS

| | | | |
|---|---|---|---|
| 2005/0139506 A1* | 6/2005 | Lorenzato | A61J 7/04 206/534 |
| 2005/0150806 A1* | 7/2005 | Lorenzato | A61J 7/04 206/534 |
| 2005/0183982 A1 | 8/2005 | Giewercer | |
| 2005/0267356 A1* | 12/2005 | Ramasubramanian | G06F 19/3462 600/411 |
| 2005/0280257 A1* | 12/2005 | Nijjer | B42D 5/04 283/2 |
| 2007/0023318 A1* | 2/2007 | Mauk | A61J 7/0084 206/570 |
| 2008/0027291 A1 | 1/2008 | Williams-Hartman | |
| 2008/0054007 A1* | 3/2008 | Mador | A61J 7/0481 221/1 |
| 2008/0077439 A1 | 3/2008 | Guion | |
| 2008/0162188 A1 | 7/2008 | Kripalani et al. | |
| 2008/0312965 A1* | 12/2008 | Meshginpoosh | G06F 19/322 705/3 |
| 2008/0312966 A1* | 12/2008 | Meshginpoosh | G06Q 50/22 705/3 |
| 2009/0039640 A1* | 2/2009 | Nijjer | B42D 5/04 283/2 |
| 2009/0299522 A1 | 12/2009 | Savir et al. | |
| 2010/0206765 A1* | 8/2010 | Fonte | A61J 7/04 206/534 |
| 2013/0002795 A1* | 1/2013 | Shavelsky | A61J 7/04 348/14.01 |
| 2013/0018503 A1* | 1/2013 | Carson | B65B 57/16 700/216 |
| 2013/0030566 A1* | 1/2013 | Shavelsky | A61J 7/04 700/244 |

\* cited by examiner

FIG. 3

COMPLIANCE GUIDE FOR DAVE MICELI

To use this guide, please note the depiction of one of the daily pill tray sections and the four compartments. This includes all the medications to be placed in each daily section.

METFORMIN HYDROCHLORIDE 500mg TAB
Take 1 tablet in the morning and 1 tablet in the evening with food.
*MAY CAUSE NAUSEA*
*TAKE WITH FOOD.*
*MAY CAUSE METALLIC AFTER TASTE.*

LISINOPRIL-HCTZ 10/12.5 TAB.
Take 1 tablet once a day.
*WARNING: IF YOU BECOME PREGNANT DO NOT TAKE THIS DRUG*
*MAY CAUSE DIZZINESS.*
*MAY CAUSE A DRY COUGH. IF THE DRY COUGH PERSISTS OR BECOMES DISTRESSING, REPORT TO YOUR DOCTOR.*

PROPRANOLOL 40mg TAB
Take 1 tablet in the morning. Take 1 tablet at noon. Take 1 tablet in the afternoon and 1 tablet in the evening as prescribed by your physician.
*THIS DRUG MAY REDUCE BLOOD FLOW TO YOUR HANDS AND FEET, CAUSING THEM TO FEEL COLD.*
*SMOKING MAY WORSEN THIS EFFECT. DRESS WARMLY AND AVOID TOBACCO USE.*
*DIZZINESS, LIGHTHEADEDNESS, OR TIREDNESS MAY OCCUR AS YOUR BODY ADJUSTS TO THE MEDICATION.*
*NAUSEA/VOMITING, STOMACH PAIN, VISION CHANGES, TROUBLE SLEEPING, AND UNUSUAL DREAMS MAY OCCUR.*

ATORVASTATIN CALCIUM 20 mg TAB
Take 1 tablet by mouth every day
*AVOID CONSUMING GRAPEFRUIT OR GRAPEFRUIT JUICE WHILE ON THIS MEDICATION. CONSULT WITH YOUR PHARMACIST OR DOCTOR ABOUT USING THIS MEDICATION IF YOU ARE PREGNANT, PLAN TO BECOME PREGNANT, OR IF YOU ARE BREASTFEEDING*

AM
1 x METFORMIN 500mg
1 x ATORVASTATIN 20mg
1 x LISINOPRIL 20mg
1 x PROPRANOLOL 40mg

NOON
1 x PROPRANOLOL 40mg

PM
1 x METFORMIN 500mg
1 x PROPRANOLOL 40mg

EVENING
1 x PROPRANOLOL 40mg

Mark off each day as you take your medication. Tear off and turn in to your pharmacy when you have taken your 30-day supply of medication.

FIG. 4

COMPLIANCE PILL TRAY SYSTEM

CROSS-REFERENCE TO RELATED APPLICATIONS

This application is a continuation-in-part to co-pending U.S. application Ser. No. 14/304,204 filed Jun. 13, 2014, and entitled "Compliance Calendar System for Pharmaceutical Container," which is a continuation-in-part to co-pending U.S. application Ser. No. 13/746,671 filed Jan. 22, 2013, and entitled "Compliance Label System For Pharmaceutical Container."

FIELD

This disclosure relates generally to a compliance system for prescription medications. More particularly, this disclosure relates to such a compliance system having a pill tray and associated calendar for the purpose for improving patient compliance in taking prescription medication by assisting the user in accurately dosing the pill tray and in keeping track of their compliance.

BACKGROUND

Compliance in regards to the taking of prescription medication is the degree to which a patient correctly follows the doctor's directions in taking medication. One problem observed with the use of prescription medications is a low level of compliance by patients in taking the medications as directed. For example, in the case of the brief instructions "take one tablet per day," it has been observed that patients often do not take a tablet each day, or, if they do, the timing of the taking of the medication is not appropriately spaced. Appropriate spacing in this case would be one tablet every twenty-four hours. However, while a patient may typically take the tablet at the same time each day during the week, such as at 8 am, on the weekend, the patient may sleep later and be out of their weekday routine. This can result in the patient either forgetting to take the tablet or else taking it much later in the day. This undesired schedule for taking the medicine could have adverse affects to the patient. Also, it is not uncommon for a patient to take their medicine, but forget later whether or not they actually took their medicine. This is especially common if a patient is to take a medication several times per day and/or multiple medications per day, as increased medications and frequency of each medication represents increased opportunities to fail to comply or to forget whether or not they complied.

Various approaches have been taken in an effort to improve patient compliance in taking prescription medication. For example, U.S. Pat. No. 7,907,477 describes a timer to be applied to a cap for a prescription container for improving compliance. U.S. Pat. No. 5,014,798 describes a cap for a prescription container having a computer chip for monitoring of patient usage. U.S. Pat. No. 6,574,165 describes a pill dispenser having a timer configured to ring an alarm when a medication is to be taken. The various attempts to improve compliance such as the above have various disadvantages in terms of expense, complexity, and acceptability to the patient. For example, generally speaking, the persons who are most likely to need prescription medication and to be non-compliant are over the age of about fifty and, in many cases, are on fixed incomes or insurance plans that are limited in coverage. This group is generally less likely to adapt to compliance methods involving more complex and expensive technology.

Another approach, as disclosed in U.S. Patent Publication Nos. 2004/018898 and 2008/0077439, is to provide the customer with a calendar in conjunction with a prescription where the calendar provides information as to when the patient should take a prescribed medication. As broadly disclosed in these references, the calendar could be applied as a label on the pharmaceutical container or provided as a separate sheet accompanying the prescription container. However, while offering a calendar is inexpensive to implement and generally easy to explain and use, the calendar systems disclosed in these references are ineffective for several reasons. In particular, as noted above, compliance issues are particularly common when multiple medications are prescribed, but the calendars disclosed in these applications are intended for only one medication dispensed in a standard prescription container. Thus, if a patient were prescribed multiple medications at one time, the patient would have to keep track of multiple calendars. Further, the calendars do not correspond particularly to the containers. Thus, there is nothing that encourages interaction between the patient and the compliance calendar.

Accordingly, other approaches have been taken in an effort to improve compliance with respect to patient's that are prescribed multiple medications. Many of these approaches include dosing medications into a plurality of compartments corresponding to pre-assigned times to take the medications. For example, U.S. Pat. No. 5,159,451 describes a medicine reminder cabinet for dosing prescribed medications into separate compartments and including means for automatically dispensing the medications from the cabinet at appropriate times. Similarly, U.S. Pat. No. 5,826,217 describes a programmable medicine dispenser in which a medication administration schedule is programmed into the dispenser and a medication compartment is automatically opened upon acknowledgement of a user of an alarm instructing the user to take a scheduled dosage. Similar to the expense, complexity, and acceptability issues of the mechanical mechanisms described above with respect to singular prescriptions, patients are not likely to adapt to automated dispensers such as the above. Further, these types of machines often require complex counters and dispensing mechanisms that must be designed to accept and dispense differently sized and shaped pills. Such mechanisms often break down causing inaccurate dosing and/or broken or crushed medications. Additionally, such designs are generally bulky and lack portability, which is heavily desired in allowing the user to take their medications with them as they go about their daily routine.

In view of the above, traditional pill trays are still the most commonly used tool for compliance in taking multiple prescriptions because they are generally simple, portable, and inexpensive. Further, despite their simplicity, they are believed to be quite effective based, at least in large part, on the user going through the process of manually dosing the individual compartments. However, problems still persist with typical pill trays in that they must first be dosed accurately. Further, a user must still remember to take the appropriate doses at the appropriate times. In this respect, various approaches have been taken to improve traditional pill trays.

For example, U.S. Pat. No. 8,174,370 discloses an automated pill tray reminder device where each compartment of the pill tray includes an integrated light pipe that is selectively illuminated for alerting the user to consume a preselected dosage in the compartment. While the pill tray device of the '370 Patent includes a cover for applying a plurality of separate labels "used to describe particular dosages," the labels do not correspond in any way to the compartments of the pill tray. In fact, the cover allows for placement of 16 labels divided into two columns while the pill tray includes 28 separate compartments divided into a table with 7 columns and 4 rows. Accordingly, the separate labels to be applied to the cover of the pill tray of the '370 Patent do not effectively assist in dosing the pill tray. Further, the pill tray of the '370 Patent would still be expensive to manufacture due to its complex lighting structure. Finally, the pill tray of the '370 Patent does not provide a system for monitoring past compliance other than a pill tray compartment being empty indicating that the patient took the medication in that compartment. Relying simply on empty compartments to determine compliance is problematic for several reasons including the fact that the patient may not remember whether the earlier compartment was even dosed or dosed correctly.

U.S. Pat. No. 6,550,618 provides another improved pill tray in which an information card is secured to the pill tray. As shown in FIG. 2, each information card requires three critical elements: 1) a photograph of each medication to be taken by the patient; 2) for each medication, a weekly graphical representation of the medications as they should be dosed into the particular compartments of the pill tray; and 3) a duplicate of the prescription label that would, as required by law, already be included on the container in which the medication would have been dispensed. These elements are provided in a row format wherein each row includes information for only one of the medications. Accordingly, while the '618 Patent provides information to assist in dosing the pill tray, the information card is extremely convoluted particularly in cases where the patient is prescribed more than two or three medications. In fact, as pointed out in the background of the '618 Patent, it is common for patients to be prescribed five or more medications. However, the figures depict at most four medications being able to be provided on a full sheet of paper, which then must be attached to the tray in an awkward and clumsy way. Thus, multiple information cards would be needed for more than a couple of medications unless the information is provided in very small print, which is obviously undesirable. Further, when the information card is provided in a more desirable position such as the inside surface of a cover for the pill tray as shown in FIG. 5, the information card must be even smaller further reducing the number of medications that can be shown on one card.

Additionally, it is believed by the assignees of the disclosure herein that pictorial representations of drugs are at most nominally beneficial as many tablets for various medications are sized and shaped very similarly. Finally, providing a prescription label for each drug on the prescription card is redundant because a correct and simplified graphical representation should already identify the pharmaceutical and provide the correct dosage information. In summary, too much information on the information card as disclosed in the '618 Patent is just as bad as too little information. Just like prescription labels applied to a prescription container, visible space on the information card must be maximized with important information laid out in an effective manner such that the user easily understands the information presented and is able to intuitively and accurately dose the pill tray each and every time. The disclosure of the '618 Patent fails to do so in a convenient and effective manner.

Solving the above and other needs, the present disclosure provides a compliance system that is inexpensive to implement and promotes continuous and consistent compliance of multiple medications using a pill tray.

SUMMARY

The disclosure advantageously provides a prescription compliance system for improving patient compliance in taking a plurality of prescribed medications each having prescription instructions instructing a user to take the prescribed medication at prescribed times. The prescription compliance system includes a pill tray including a base portion having a pill tray layout including a plurality of frequency sections and a plurality of sequence compartments within each frequency section and a compliance calendar having a calendar layout including a plurality of frequency reminders and a plurality of sequence reminders within each frequency reminder to provide a plurality of demarcated sequence sections. Each of the plurality of demarcated sequence sections correspond to one of the plurality of sequence compartments of the pill tray and has dosing instructions including identification of the plurality of prescribed medications that should be dosed to the corresponding sequence compartment of the pill tray according to the prescription instructions of the plurality of prescribed medications.

In preferred embodiments, the pill tray is a weekly pill tray such that each of the plurality of frequency sections corresponds to a particular day of the week and each of the plurality of sequence compartments of each frequency section corresponds to a particular time of day to take the prescribed medication during the particular day of the week. Additionally, each of the plurality of frequency sections is operable to be removed from the base portion independently of other frequency sections.

In preferred embodiment, the positioning of the demarcated sequence sections of the calendar layout substantially mimics positioning of the sequence compartments in the pill tray layout. Further, the pill tray includes a cover operable to move between an open position and a closed position, and the compliance calendar is dimensioned and configured to be secured to the cover of the pill tray such that the compliance calendar is visible to a user when the cover is in the open position. An advertisement may be secured to the cover of the pill tray such that the advertisement is visible to the user when the cover is in the closed position.

According to certain embodiments, the cover is composed of a clear plastic and the compliance calendar is printed on a first side of a sheet material and the advertisement is printed on a second side of the sheet material, the sheet material being configured to be secured to the cover such that the first side is visible to the user when the cover is in the open position and the second side is visible to the user when the cover is in the closed position.

According to certain embodiments, the pill tray includes an electronic display for displaying the compliance calendar to the user and the pill tray is in communication with a pharmacy computer system for receiving the compliance calendar in an electronic format to be displayed on the electronic display.

According to another embodiment of the disclosure, a prescription compliance system is provided for improving patient compliance in taking a plurality of prescribed medications each having prescription instructions providing that the prescribed medication is to be taken according to a particular sequence schedule each day. The prescription compliance system includes a pill tray including a base portion having a plurality of daily sections and a plurality of sequence compartments within each daily section, the plurality of sequence compartments configured for receiving the plurality of prescribed medications according to the sequence schedule of each of the plurality of prescribed medications. The system further includes a compliance calendar including only one daily reminder having a plurality of sequence reminders to provide a plurality of demarcated sequence sections each corresponding to one of the plurality of sequence compartments within each daily section of the pill tray. Each of the plurality of demarcated sequence sections have dosing instructions including identification of the plurality of prescribed medications that should be dosed to the corresponding sequence compartments of the pill tray according to the prescription instructions of the plurality of prescribed medications.

In certain embodiments, the compliance calendar is provided to the user as a sheet material, and the sheet material further includes a second compliance calendar including at least a plurality of daily reminders corresponding to a prescription period for recording when the user complied with the prescription instructions. In certain embodiments, the second compliance calendar is operable to be removed from the sheet material for record keeping of compliance. In other embodiments, both compliance calendars are operable to be removed from the sheet material together for record keeping of compliance.

According to yet another embodiment of the disclosure, a method for improving patient compliance in taking a plurality of prescribed medications each having prescription instructions providing that the prescribed medication is to be taken each day according to a sequence schedule is provided. The method includes providing a pill tray to a patient including a base portion having a plurality of daily sections and a plurality of sequence compartments within each daily section, the plurality of sequence compartments configured for receiving the plurality of prescribed medications according to the sequence schedule of each of the plurality of prescribed medications; dispensing each of the plurality of prescribed medications to the patient; and providing a compliance calendar to the patient, the compliance calendar including at least one frequency reminder having a plurality of demarcated sequence sections corresponding to the plurality of sequence compartments within each daily section, each of the plurality of demarcated sequence sections including dosing instructions including identification of the plurality of prescribed medications that should be dosed to the corresponding sequence compartments of the pill tray according to the prescription instructions of the plurality of prescribed medications.

According to certain embodiments, the pill tray includes a cover composed of a clear material operable to move between an open position and a closed position, the compliance calendar is provided on a first side of a compliance sheet, and an advertisement is provided on a second side of the compliance sheet. The compliance sheet is dimensioned and configured to be removeably secured to the cover of the pill tray such that the compliance calendar is visible to the patient when the cover is in the open position and the advertisement is visible to the user when the cover is in the closed position. The step of providing the pill tray to the patient may then include a pharmacy providing the pill tray to the patient at a reduced cost by selling advertising space on the second side of the compliance sheet to third parties.

According to certain embodiments, the compliance calendar is disposed on a compliance sheet and the method further includes instructing the patient to record compliance in taking the plurality of prescribed medications directly on the compliance sheet.

In some embodiments, the compliance calendar includes only one frequency reminder and the compliance sheet further includes a second compliance calendar having at least a plurality of frequency reminders with no dosing instructions for recording compliance in taking the plurality of prescribed medications directly on the compliance sheet. The second compliance calendar may then be operable to be removed from the compliance sheet.

According to certain embodiments, the step of providing the compliance calendar to the patient includes transmitting the compliance calendar from a pharmacy computer system to a customer computer system. The customer computer system may include an electronic display operable to be secured to the pill tray for displaying the compliance calendar to the patient. In certain embodiments, the electronic display has a touch screen for displaying the compliance calendar to the patient and the compliance calendar is interactive for recording compliance in taking the plurality of prescribed medications directly on the electronic display. The method may then include transmitting the recorded compliance from the customer computer system to the pharmacy computer system.

BRIEF DESCRIPTION OF THE DRAWINGS

Further advantages of the disclosure are apparent by reference to the detailed description in conjunction with the figures, wherein elements are not to scale so as to more clearly show the details, wherein like reference numbers indicate like elements throughout the several views, and wherein:

FIG. 3 depicts a first side of a compliance sheet having a compliance calendar according to one embodiment of the disclosure;

FIG. 4 depicts a first side of a compliance sheet having a compliance calendar according to another embodiment of the disclosure;

DETAILED DESCRIPTION

A prescription compliance system is provided that utilizes a pill tray and associated compliance sheet. While the compliance system may be utilized for singular prescriptions, it is particularly useful when a patient is prescribed multiple medications taken in various dosages at various times of the day. In particular, there is currently a big push by pharmacies to convert customers taking multiple drugs to a system known as "Medication Synchronization" or "Med Sync." This involves filling every maintenance or normal script for patients for a set time period (typically a monthly prescription period) so that the prescription for each drug needs to be refilled on the same day. This greatly simplifies picking up prescriptions for the customers or delivering the prescriptions to the customers, and it also ensures that the pharmacies get a set number of refills regardless of whether the patient is actually taking the medications as prescribed. However, while supplying the prescriptions to the customers each month might impact the patient's compliance, there is no direct link between delivering the prescriptions consistently and the patient taking the medications consistently. Thus, the below system is particularly suited to being used in conjunction with a medication synchronization program where the pharmacy is aware of the dosage information for each medication being taken by the patient. Alternately, a third party could receive information regarding the patient's prescriptions from either the patient or the pharmacy, and implement the prescription compliance system of the present disclosure for the patient. In particular, the third party could provide the pill tray and associated compliance sheets described below in the same role as the pharmacy except for the fact that the third party is not actually dispensing the prescriptions to the patient.

In operation, the compliance sheet is configured to assist the user, typically a patient or the patient's caregiver, in easily and accurately dosing the patient's prescribed medications into the pill tray. Together, the pill tray and compliance sheet remind a patient how and when to take the medications every time the patient handles the prescription pill tray or components thereof. Further, the compliance sheet is intended to remain with the pill tray to aid the patient in keeping track of their compliance. As explained below, the synergistic effect of the pill tray and compliance sheet provides a simple, compact, and low-cost system for improved patient compliance in taking prescription medications.

Figure 1A:
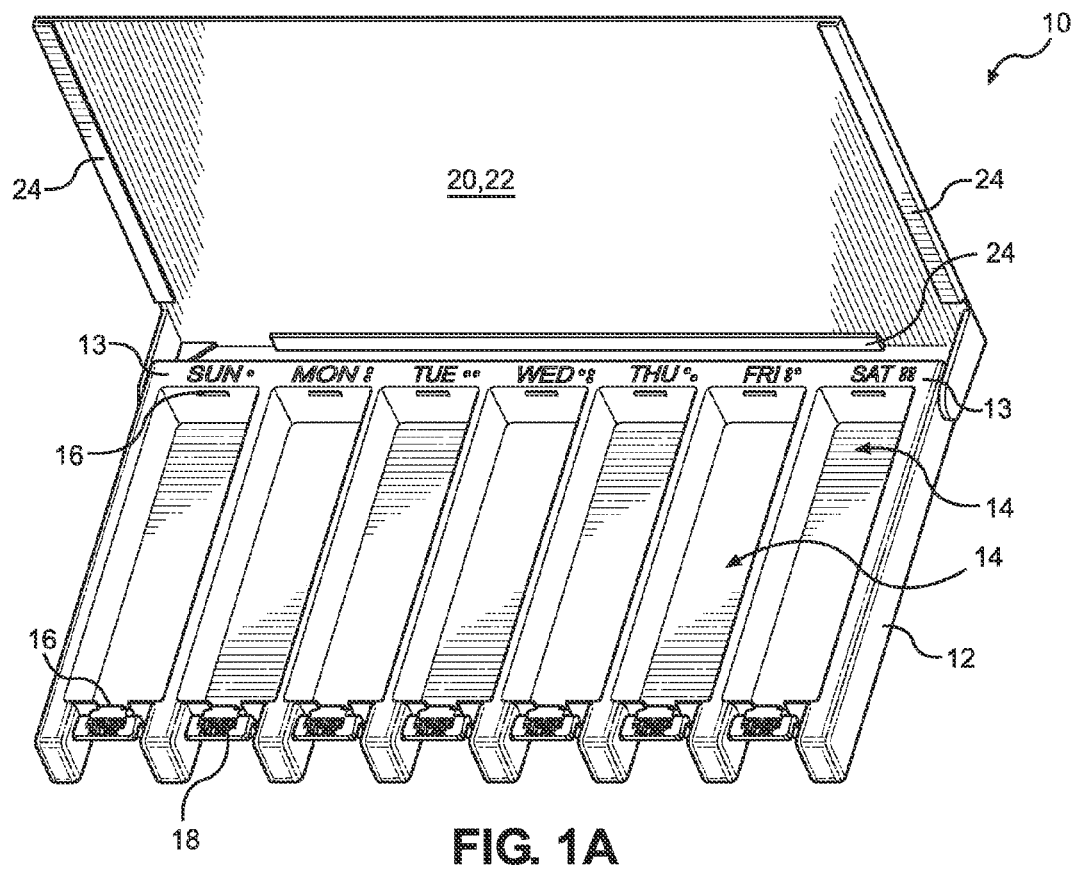
FIGS. 1A-1B depict a perspective view of a pill tray having removeable frequency sections according to one embodiment of the present disclosure.
Figure 1B:
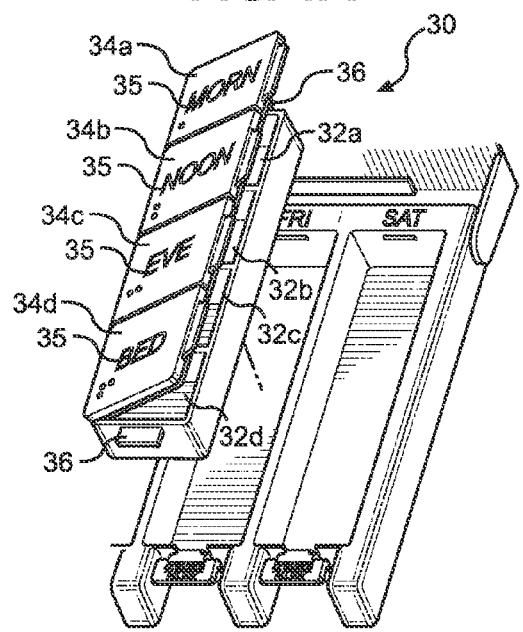
Figure 2:
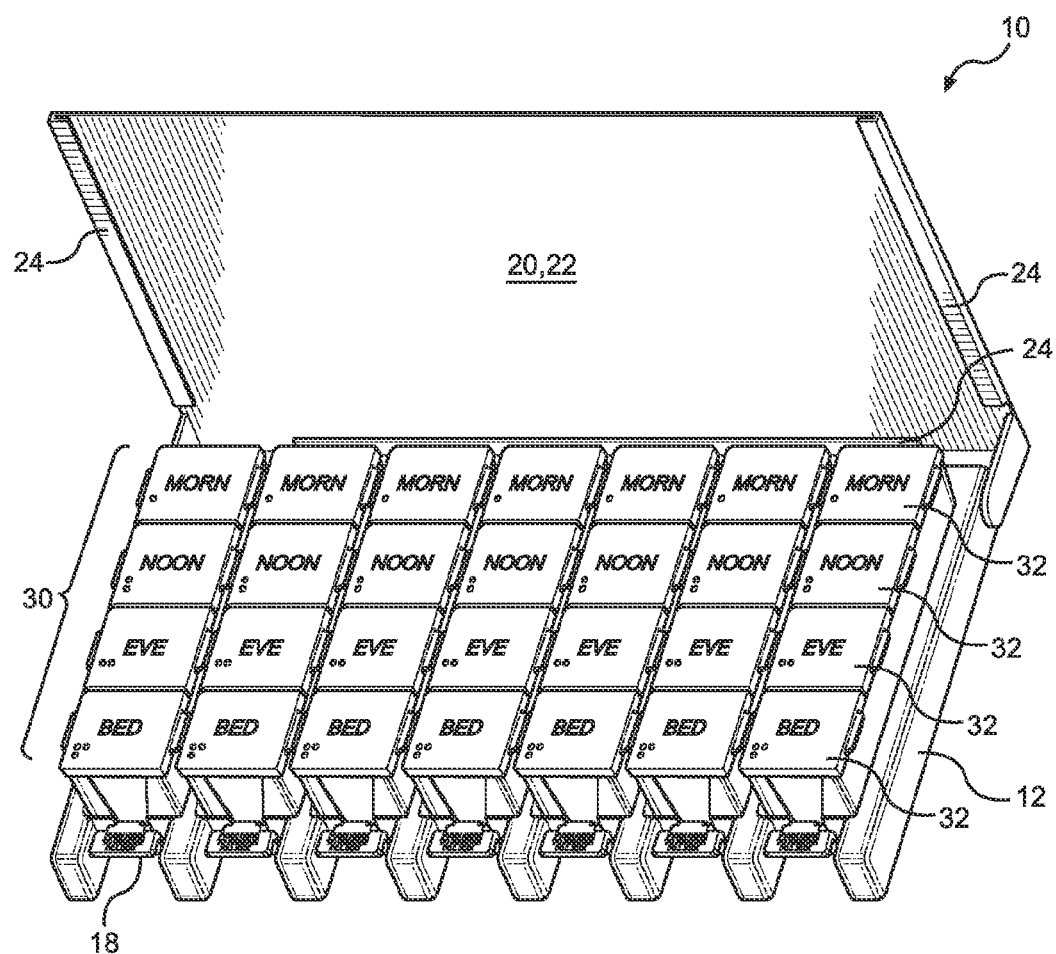
FIG. 2 depicts a perspective view of the pill tray of FIGS. 1A-1B with the removeable frequency sections secured to the pill tray according to one embodiment of the disclosure.

With initial reference to FIGS. 1A-1B and FIG. 2, there is shown a pill tray 10 preferably having three main components: a base portion 12, a cover 20, and a plurality of removeable pill tray sections 30. The base portion 12 includes a plurality of cavities 14 for receiving the pill tray sections 30. Each cavity 14 includes engaging mechanisms 16 that correspond to engaging mechanisms 36 of the pill tray sections 30 such that the sections 30 may be removeably secured to the appropriate cavity 14 of the base portion 12. As shown, the cavity engaging mechanisms 16 are preferably slots and the pill tray section engaging mechanisms 36 are preferably tab elements sized and configured to engage the slots 16. To assist a user in removing the sections 30, each cavity 14 is preferably provided with a release tab 18 for pushing the section tab elements 36 out of the slots 16. The pill tray sections 30 are preferably removeable to provide additional convenience in going about the patient's daily affairs. In other words, if desired, the patient can remove a pill tray section 30 corresponding to one day of prescribed medications from the already compact pill tray 10 to take just the daily section 30 as the patient goes about their day.

In preferred embodiments, the pill tray 10 is a weekly pill tray and, thus, the base portion is configured to receive seven separate daily pill tray sections 30. Further, referring particularly to FIG. 1B, the daily sections 30 are preferably further separated into a plurality of sequence compartments 32 corresponding to the different times the user takes their prescribed medications during the day. As shown, the daily section 30 of the preferred embodiment is divided into four sequence compartments 32a-32d corresponding to four separate times of the day such as AM, NOON, PM, and EVENING. Each sequence compartment 32 includes a lid 34a-34d preferably hingedly connected to the respective sequence compartment 32a-32d for opening and closing the particular sequence compartment 32. Each lid 34a-34d preferably includes indicia 35 indicating the time of day to which the sequence compartment 32a-32d corresponds. While not preferred, in certain embodiments each sequence compartment 32a-32d may be further configured to be removeable from the daily sections.

While the pill tray 10 is shown and described above as a weekly pill tray for receiving seven daily sections 30, it should be understood that the tray could be configured to receive any number of sections 30 as desired. Further, the sections 30 may also correspond to other frequencies in which prescribed medications are to be taken such as every twelve hours, two days, weekly, etc. Accordingly, while the term "daily sections" is generally used in describing preferred embodiments of the disclosure, the daily pill tray sections 30 may be more broadly referred to herein as "frequency sections," with the sequence compartments 32 of the frequency sections 30 then corresponding to particular times to take the prescribed medications during each frequency.

Figure 8:
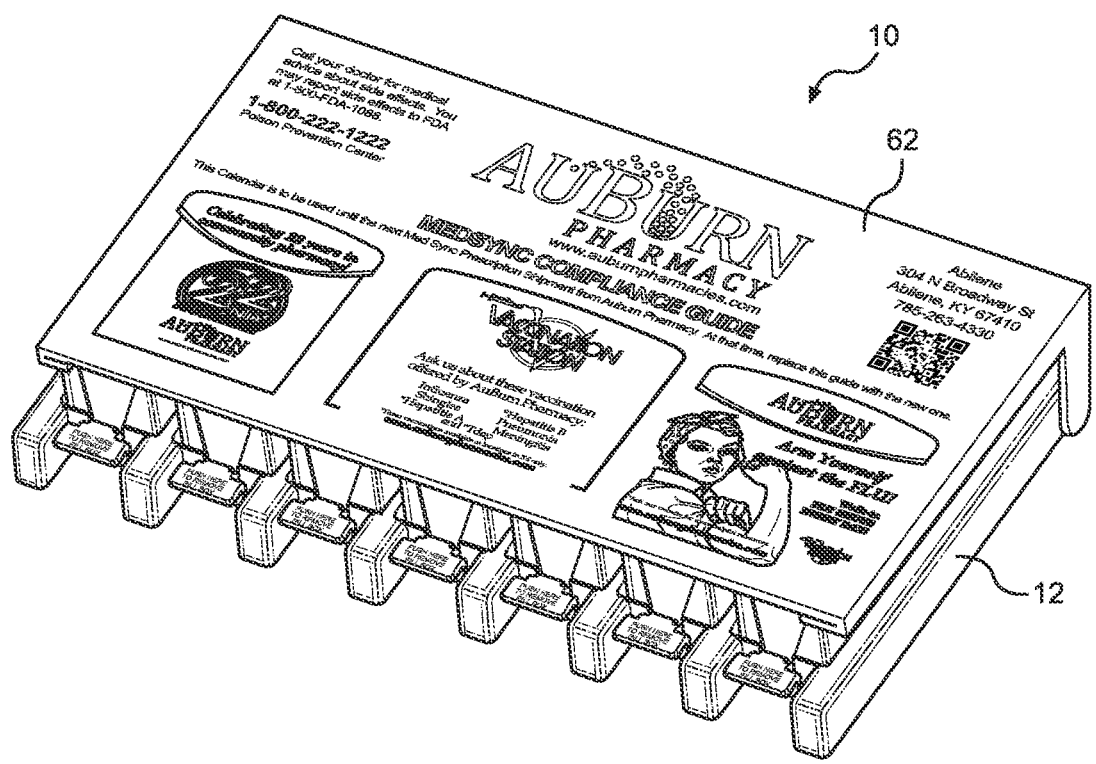
FIG. 8 depicts a perspective view of the pill tray of FIG. 2 with the cover of the pill tray in a closed position and the second side of the compliance sheet of FIG. 6 being visible to the user.

The cover 20 is connected to the base portion 12 such that it is operable to move from an open position (FIG. 2) to a closed position (FIG. 8). As shown, the cover 20 is preferably hingedly connected to a top end 13 of the base portion 12 such that an inside surface 22 of the cover 20 is visible when the cover 20 is in the open position. In this embodiment, the inside surface 22 of the cover 20 further includes a plurality of slots 24 for removeably receiving a compliance sheet as described below that is visible to the user when the cover 20 is in the open position. When the cover 20 is moved to the closed position, the cover 20 assists in preventing the frequency sections from popping out of the base portion 12 and/or the lids 34 of the sequence compartments 32 from unintentionally opening.

It should be understood that other configurations for connecting the cover 20 to the base portion 12 are possible and within the scope of the present disclosure. For example, the base portion 12 could include slots on the sides or ends of the base portion for receiving corresponding tab elements extending from the inside surface 22 of the cover 20 such that the cover slides to the open and closed position as opposed to a hinged connection. Further, the compliance sheet 50 could be secured to the cover 20 in a number of alternative ways such as clips, magnets, adhesive, etc. In preferred embodiments, however, the attachment mechanisms for securing the sheet 50 to the cover 20 permit the sheet 50 to be easily removed from the cover 20 and replaced with a new compliance sheet following a particular prescription period or as otherwise needed.

Figure 3:
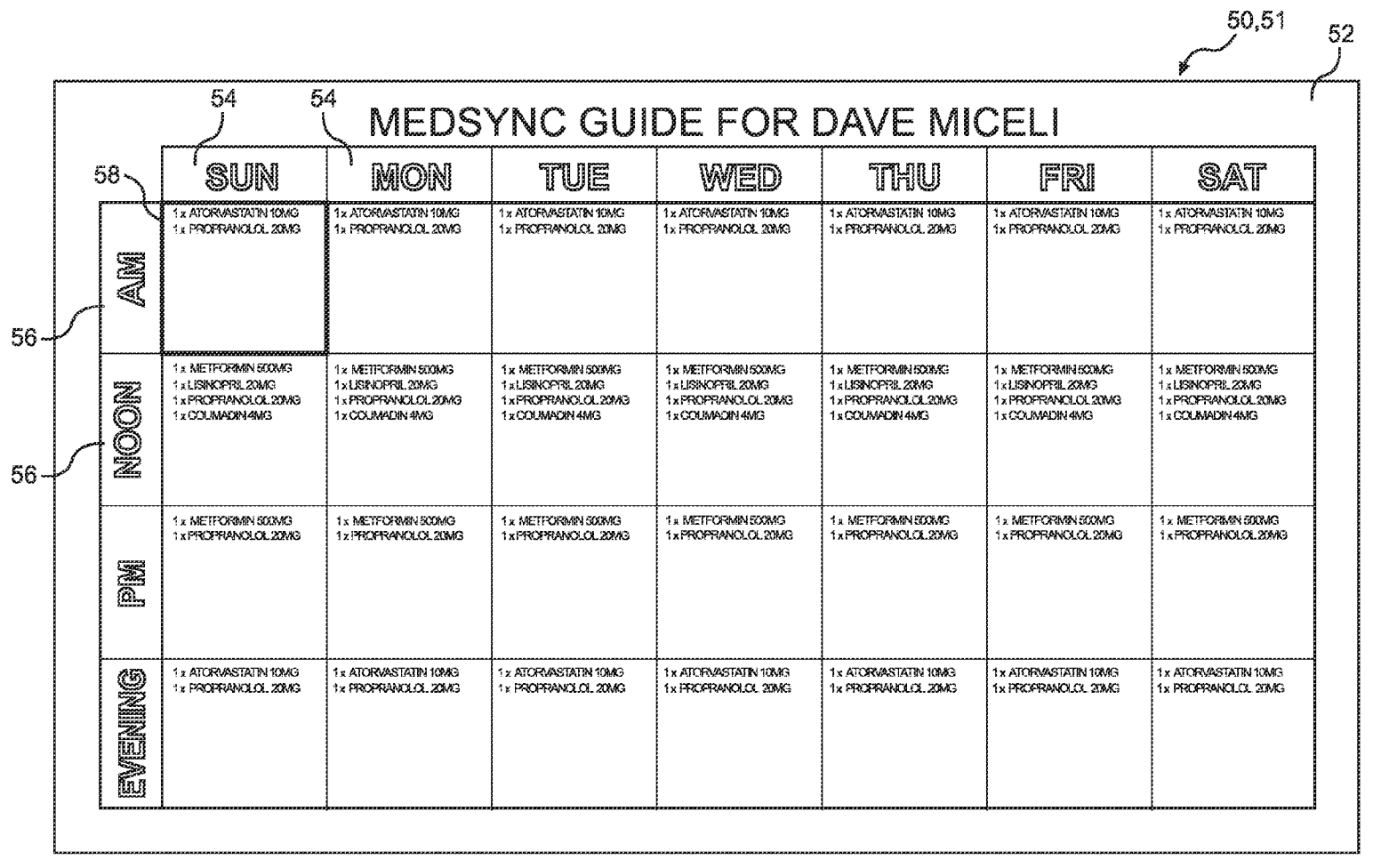

Referring to FIG. 3, there is shown a compliance sheet 50 having a compliance calendar 52 thereon. While compliance calendar 52 is referred to herein as a "calendar," the calendar 52 may take many forms with the critical aspect being that it provides graphical dosage instruction information relating to prescribed medications to be used by the patient in dosing the sequence compartments 32 of pill tray 10. As such, the calendar 52 is configured to facilitate compliance by the patient in taking the prescribed medication as directed. It will be appreciated that the dosage instruction information provided by the compliance calendar 52 is configured to correspond to the prescription medications being taken by the patient and the physician's instructions for taking the medicine. Accordingly, the calendar 52 includes at least one frequency reminder 54 and a plurality of sequence reminders 56 of the times to take the medication during each frequency.

For example, with respect to calendar 52 of FIG. 3, the prescribed medication is ATORVASTATIN 10 MG, PROPRANOLOL 20 MG, METFORMIN 500 MG, LISINOPRIL 20 MG, COUMADIN 4 MG. With respect to ATORVASTATIN, the prescription provides that one tablet should be taken twice per day by the patient with one tablet being taken in the morning and one tablet in the evening. With respect to PROPRANOLOL, the prescription provides that one tablet should be taken four times a day. As for METFORMIN, one tablet should be taken at both noon and in the afternoon. Finally, both the LISINOPRIL and COUMADIN prescriptions require the patient to take one tablet per day at noon. The dosage instruction information with respect to these prescribed medications are provided on the calendar 52 in the form of a plurality of frequency reminders 54 corresponding to each day and sequence reminders 56 corresponding times to take the medications during each day. The frequency reminders 54 and sequence reminders 56 are provided in a convenient format to assist the patient in properly dosing each of the sequence compartments of the pill tray 10.

In preferred embodiments, the calendar 52 is configured to mimic the pill tray 10 for providing an intuitive approach in dosing the pill tray 10. As noted above, the pill tray 10 includes a plurality of frequency sections 30 with each frequency section being further divided into one or more sequence compartments 32. The sequence compartments 32 are configured for receiving prescribed medications corresponding to prescribed times to take the prescribed medications during each frequency. Thus, according to the embodiment of FIG. 3, the calendar 52 includes a plurality of frequency reminders 54 with each frequency reminder including one or more sequence reminders 56 also corresponding to prescribed times to take the prescribed medication during each frequency.

With respect to the example of calendar 52 of FIG. 3, it is configured for use with weekly pill tray 10 having seven daily sections 30. Each daily section 30 is divided into four sequence compartments 32 corresponding to AM, NOON, PM, and EVENING. Thus, the pill tray 10 has a pill tray layout similar to a table with seven columns corresponding to days of the week and four rows corresponding to particular times of each day for a total of twenty-eight total sequence compartments 32. To mimic the pill tray layout of pill tray 10, calendar 52 includes a calendar layout also having seven frequency columns corresponding to days of the week (i.e., daily frequency reminders 54) and four sequence rows corresponding to particular times of each day (i.e., sequence reminders 56 within each day) resulting in twenty-eight demarcated sequence sections 58. As shown, each demarcated sequence section 58 in the calendar layout of this embodiment is preferably sized and positioned in substantially similar size and positioning as the corresponding sequence compartments 32 of the pill tray layout. Within each sequence section 58, specific dosing instructions are provided including an identification of each prescription drug and number of tablets that should be dosed in the corresponding sequence compartments 32 of pill tray 10.

For example, in this case, the demarcated sequence section corresponding to SUNDAY—AM includes dosing instructions for 1× ATORVASTATIN 10 MG and 1× PROPANOLOL 20 MG because the patient's prescription for ATORVASTATIN provides that one tablet should be taken twice per day by the patient with one tablet being taken in the morning and the prescription for PROPRANOLOL provides that one tablet should be taken four times a day. This provides intuitive instructions to the patient that the sequence compartment 30 of pill tray 10 corresponding to SUNDAY—AM should include one ATORVASTATIN 10 MG tablet and one PROPRANOLOL 20 MG tablet. The patient may then continue to dose the sequence compartments 32 as intuitively instructed by the calendar 52 until all sequence compartments are filled with prescribed medication as provided by calendar 52. Further, because the calendar 52 is secured to the cover of the pill tray 10 such that the calendar 52 is visible when the pill tray is in an open position, the patient may continually use the calendar 52 to confirm that a sequence compartment 32 includes the proper medication when the particular sequence of medication is being taken or when the daily section 30 is being removed from the tray 10.

It will be appreciated that the calendar 52 may be configured to correspond to any prescribed sequences. Further, the associated pill tray 10 to be used with calendar 52 may be chosen based on the physician's dosage instructions. For example, if the patient is not prescribed any medications that are taken more than twice daily, the pill tray 10 provided to the patient preferably only includes two sequence compartments 32 per frequency section 30 and the compliance calendar only includes two sequence reminders 56.

It will also be appreciated that all printed indicia of the compliance sheet 52 is preferably printed utilizing color to emphasis or highlight certain information, as may be desired. For example, different medications, days, sequences, number of tablets, etc. could be printed or highlighted in different colors to emphasize differences between the information.

In another aspect of the disclosure, the compliance calendar 52 may be utilized to maintain a log of when the patient took their medication. This maintenance of a log will advantageously enable a patient to avoid circumstances requiring them to rely on their memory for whether or not they took their medication, when particular compartments 32 should be empty or need refilling, etc. Also, it has been observed that having the patient record their compliance serves to better train the patient as to the importance of compliance, and improved compliance results are achieved. Thus, according to certain embodiments, the compliance sheet 50 includes compliance information in addition to the compliance calendar 52 instructing the patient to use a marker or pen and mark through each day or sequence as they take their medication or otherwise record when medications have been taken. Boxes may also be provided within each sequence section 58 allowing the user to check the box when the medications in the sequence compartment 30 corresponding to the particular sequence section 58 are taken.

Using the compliance sheets 50 as compliance records may also provide a record of use for the dispensing pharmacy, which can incentivize customers to bring the compliance sheets 50 back when they come in for a refill. This is important since it is expected that pharmacies will soon have to document how the steps they are taking to improve adherence and compliance are working. Pharmacies can scan the compliance sheets 50 that are returned by the patients when obtaining a refill and keep these on record for documentation for audits or to document results for payment negotiations. In the case of a medical emergency, compliance sheets 50 according to the disclosure can also function as a great reference to first responders of what medications the patient is taking and how compliant they are and have been. Thus, the calendar sheets 50 may also be provided on three hole punched paper to facilitate being kept by the patient in a binder for central retention and use, such as being readily accessible to paramedics to provide detail regarding current and past medications. Calendar sheets 50 are also helpful to maintain as medical records for use by health care professionals as they provide a quick reference of what medications are or have been prescribed to the patient and the patient's history of compliance with the prescriptions.

Referring to FIG. 4, another embodiment of compliance sheet 50 is provided in which the compliance calendar 52 includes only one frequency reminder 54. This embodiment is particularly useful when all medications prescribed to the patient are taken in the same amount and at the same times daily. In other words, each daily section 30 and associated sequence compartments 32 of pill tray 10 will include the same medications for each day of the week (e.g., SUN—AM, NOON, PM, and EVENING sequence compartments will include the same medications as the MON—AM, NOON, PM, and EVENING sequence compartments). Thus, providing a compliance calendar 52 with multiple frequency reminders 52 such as shown in FIG. 3 could be considered redundant and an inefficient use of critical space of compliance sheet 50 that could be used to provide additional compliance or prescription information as shown in FIG. 4 and described below, in particular warning information regarding the medications being taken. Accordingly, compliance calendar 52 of this embodiment preferably includes one frequency reminder 54 having four demarcated sequence sections 58 in a calendar layout that mimics the pill tray layout of only one of the daily sections 30 while providing dosing instructions for all of the sequence compartments 32 of pill tray 10. Further, as most patients take the same prescribed medications each day according to the same schedule, providing only one frequency reminder 52 on the compliance sheet 50 enables the frequency reminder 52 to be enlarged such that the dosing instructions are more easily read.

In situations in which calendar 52 includes only one frequency reminder 54, compliance sheet 50 has sufficient room to include a second compliance calendar 62 for keeping track of the patient's daily or sequence compliance. In preferred embodiments, the second compliance calendar includes a graphical representation of times in which medications are taken without including particular dosing instructions for the time periods. Due to the lack of dosing instructions, the second compliance calendar 62 includes a graphical representation where each frequency reminder or sequence section is much more compact than that of calendar 52. The more compact structure allows for the second compliance calendar 62 to include each day or sequence for the duration of the prescription period, or at least a much longer prescription period, such that there is no need to replace sheet 50 during the prescription period, or at least as frequently during long prescription periods, unless changes to the actual prescriptions are made. In preferred embodiments, the second compliance calendar 62 is provided in a more traditional calendar layout representing the particular prescription period of a medication synchronization program. Further, the compliance sheet 50 preferably includes a perforated line 64 or other means such as adhesive for removing the second compliance calendar 62 from sheet 50 to give to the pharmacy or health care professional for monitoring compliance and/or for keeping for the patient's own records. In certain embodiments, the frequency reminder 54 may also be operable to be removed with the second compliance calendar 62 making it clear which prescriptions were supposed to be taken during the prescription period.

For example, compliance sheet 50 of FIG. 4 represents a monthly medication synchronization program for a particular patient for the time period from Jul. 11, 2014-Aug. 9, 2014. Using the prescription compliance system described herein, the patient doses each daily section 30 of pill tray 10 according to the first compliance calendar 52. Then, as the patient takes each sequence or daily dosages of prescribed medications, the patient marks through or checks off the appropriate time period on second compliance calendar 62. The second compliance calendar 62 may then separated from compliance sheet 50 for record keeping of the patient's compliance.

Figure 5:
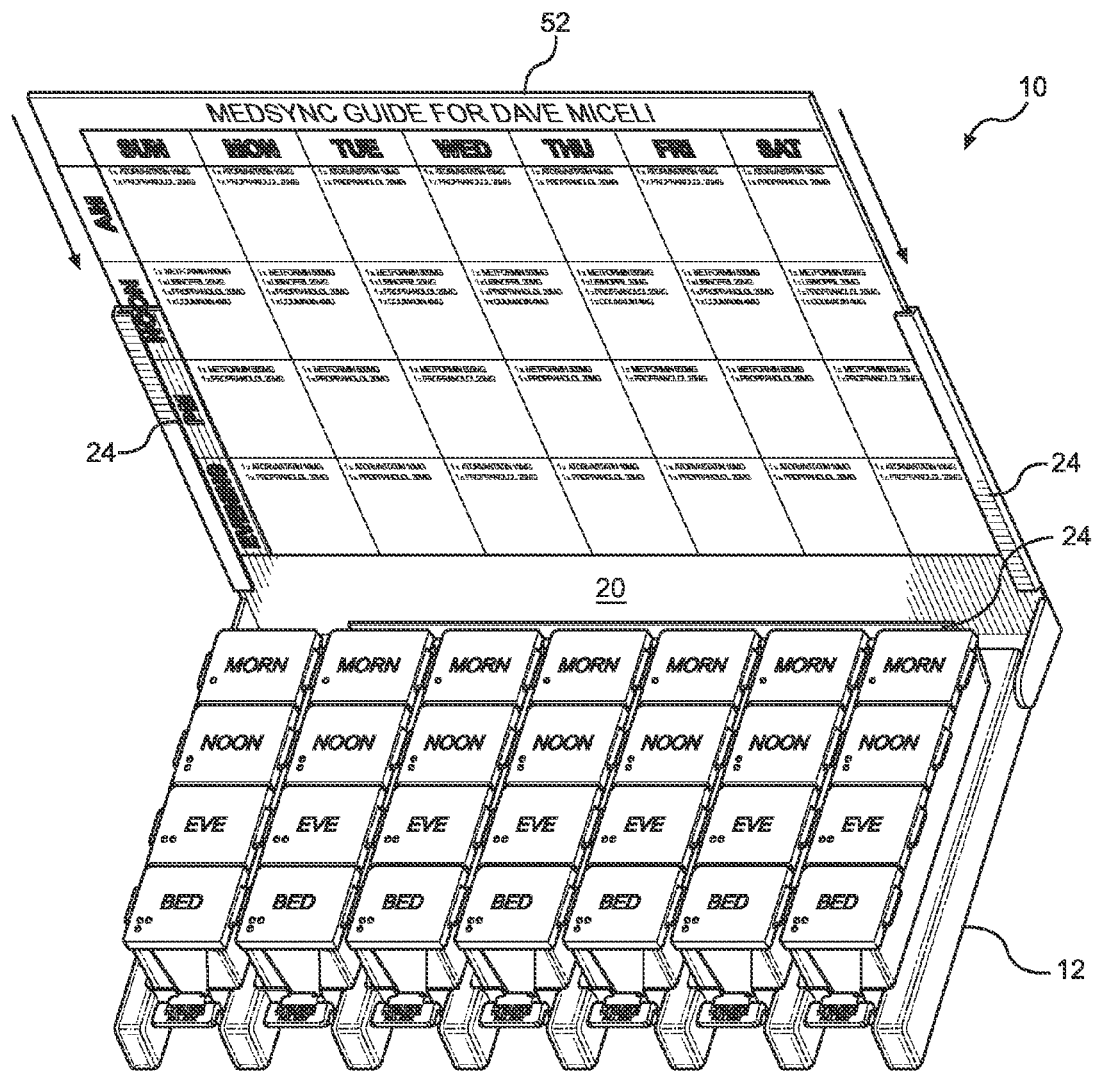
FIG. 5, depicts a perspective view of the compliance sheet of FIG. 3 being inserted into the cover of the pill tray of FIG. 2 according to one embodiment of the disclosure.
Figure 6:
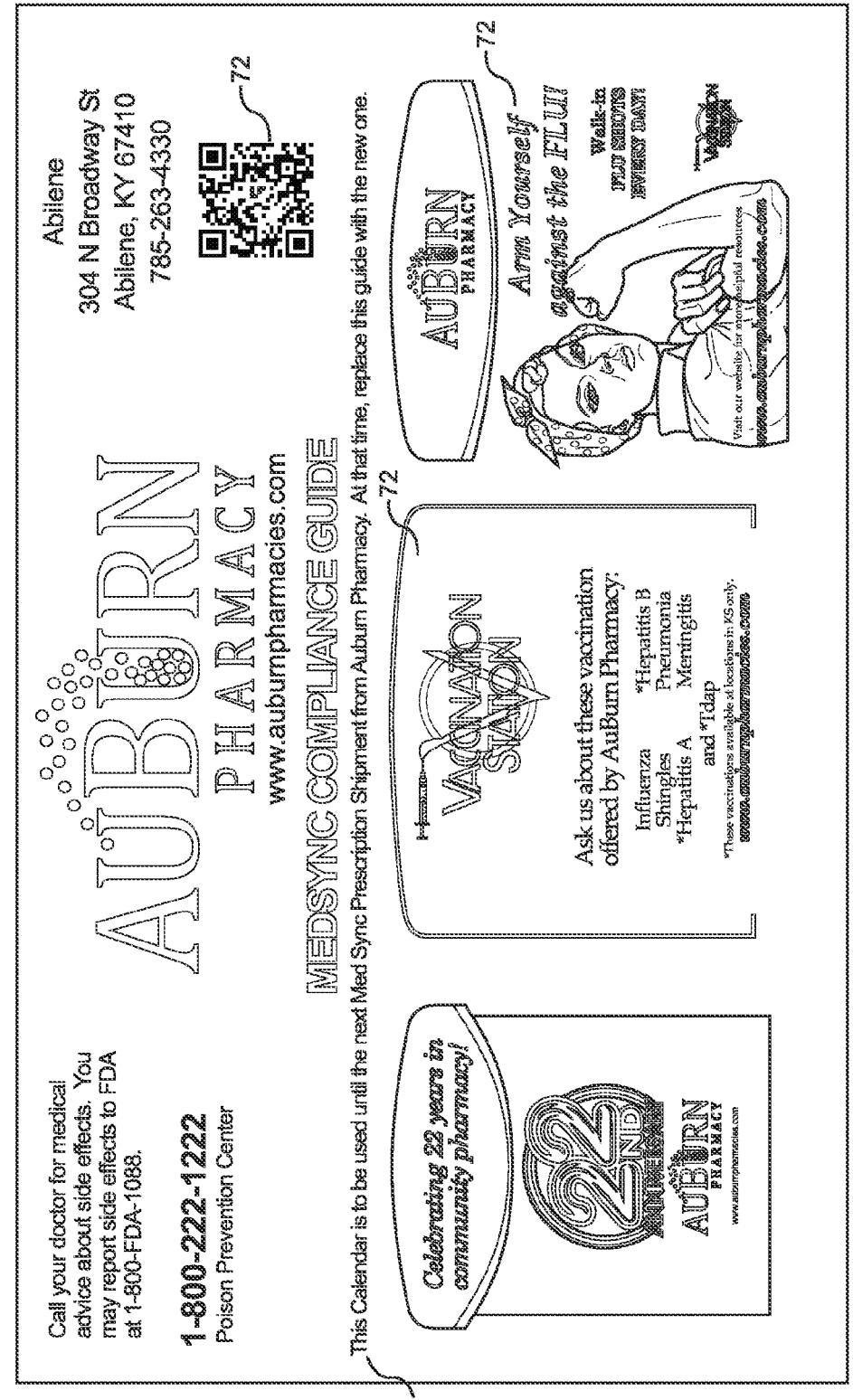
FIG. 6 depicts a second side of the compliance sheet of FIG. 3 having promotional information according to one embodiment of the disclosure.
Figure 7:
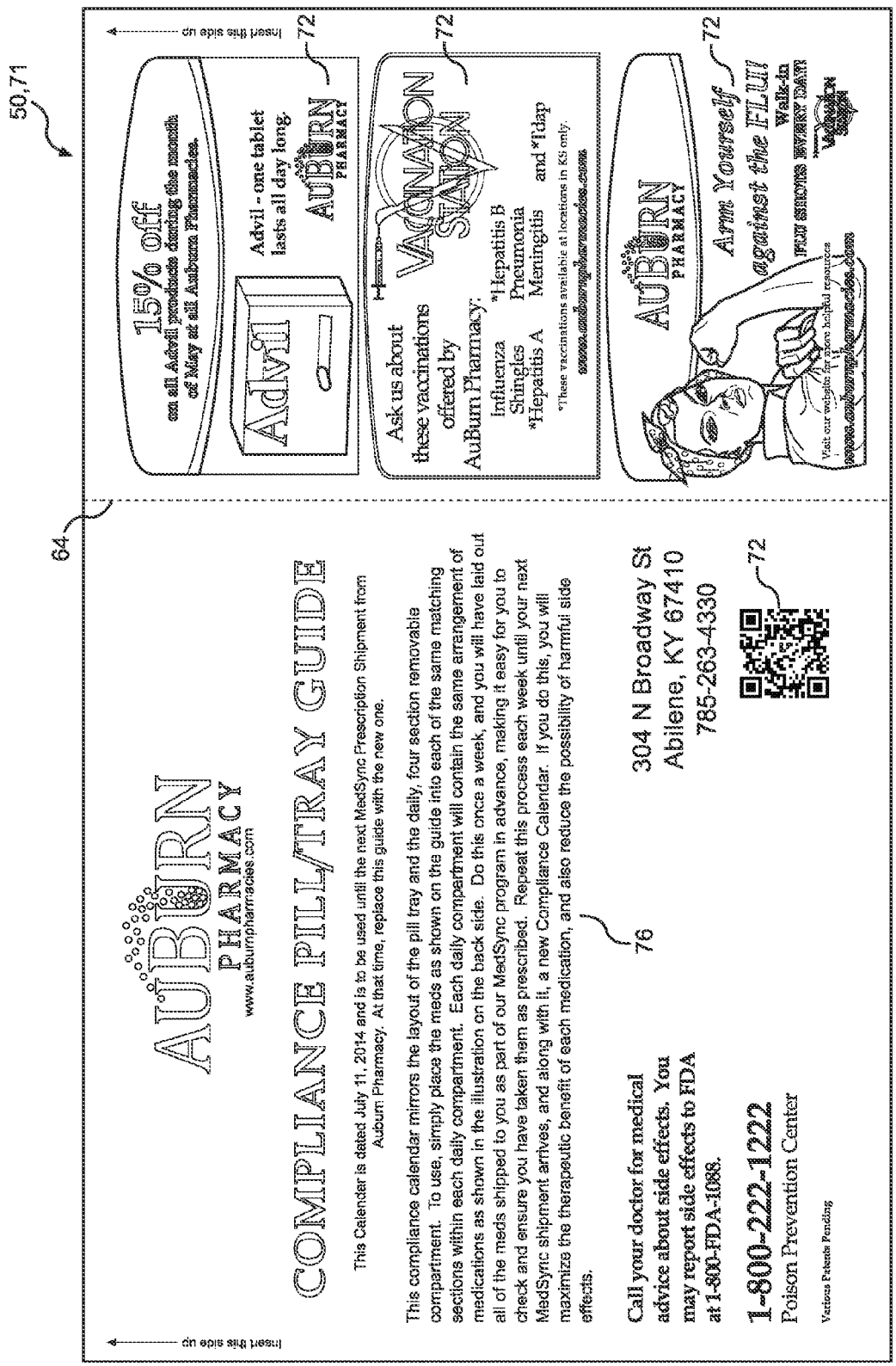
FIG. 7 depicts a second side of the compliance sheet of FIG. 4 having promotional information according to another embodiment of the disclosure.

In yet another aspect of the disclosure, compliance sheet 50 is preferably a two-sided sheet with the compliance calendar 52, and potentially second compliance calendar 62 depending on the particular embodiment of compliance calendar 52, on a first side 51 of the sheet 50 as shown in FIGS. 3-5 and additional information on a second side 71 of the sheet 50 as shown in FIGS. 6-8. In preferred embodiments, the additional information on the second side 71 of the sheet 50 includes predominantly promotional information 72. The promotional information 72 may include information directed to the dispensing pharmacy such as promotional messages regarding goods and services offered by the pharmacy, QR codes directing the user to the pharmacy's website, etc. and/or the promotional information could be directed to goods and services offered by unrelated third parties.

In preferred embodiments, the cover 20 of the pill tray is formed from an impact resistant clear plastic such as polycarbonate so that, when the compliance sheet 50 is secured to the cover 20, first side 51 of compliance sheet 50 having compliance calendar 52 is visible when the cover 20 is an open position (FIG. 5) and the second side 71 having promotional information 72 is visible when the cover is in the closed position (FIG. 8). In alternate embodiments, the promotional information 72 is provided on a sheet separate from the compliance sheet 50. In this embodiment, the color of the cover 20 is not critical and the compliance sheet 50 is preferably secured to the inside surface 22 of the cover 20 while the separate sheet having promotional information 72 is secured to the outside surface of the cover 20.

Importantly, the advertising space offered by pill tray 10 is believed to be very effective because patients and/or their caregivers will use the pill trays 10 at least daily and the compliance sheet 50 is frequently replaced following the end of prescription periods or when changes to prescribed medications are made. Thus, the pharmacy has an opportunity to frequently communicate and advertise different messages to their customers. Further, the cover 20 would be seen as prime advertising real estate due to the frequent interaction by the customer with the pill tray 10. Accordingly, the advertising may be used to subsidize the cost of the pill trays 10 to the customers or provide a source of additional revenue for the pharmacy. For example, a pharmacy may sell advertising space to a third-party, and the third-party in turn covers or subsidizes the cost of providing the pill trays 20 to the pharmacy customers. This in turn improves patient compliance because the patients receive an effective tool for achieving compliance at no or little cost that many patients may not have purchased even if the actual cost to the customer was very little without being subsidized.

In addition to the compliance calendar 52, second compliance calendar 62, and promotional information 72, compliance sheet 50 may also include instruction information 76 directed to use of the compliance sheet 50. For example, referring to FIG. 6, when the calendar 52 is a weekly calendar such as shown in FIG. 3 but is being used as part of a monthly medication synchronization program, instructions are provided to the user that "This Calendar is to be used until the next Med Sync Prescription Shipment from Auburn Pharmacy. At that time, replace this guide with the new one." Alternatively, particularly when the user is using the calendar 52 to keep track of compliance, multiple weekly calendars may be given to the patient and the instructions 76 may provide that the user should replace the calendar 52 each week with one of the replacement calendars until new calendars are given with the next shipment of prescription medications. Referring to FIG. 7, in the embodiment where the compliance calendar 52 includes only one frequency/daily reminder 54 as shown in FIG. 4, the instructions 70 may state that the daily reminder should be used to dose each daily section 30 of pill tray 10, and that the patient should use the second compliance calendar(s) 62 for keeping track of compliance, until the next fulfillment of monthly prescriptions are received along with the new compliance sheet 50.

Compliance sheet 50 may also include other compliance information such as statements as to the importance of taking the medication as directed, reminders to the patient to not skip doses, and/or why it is important to not skip doses. Information directed to the specific medications being prescribed may also be provided such as the purpose of the particular medications (e.g., in the case of statins, the purpose information informs the patient that statins are used to reduce the level of cholesterol in the blood) and warning information (e.g., "Do Not Take With Dairy" in the case of tetracycline prescriptions which are deemed less effective when taken with dairy products). Additional information may also include emergency contact information such as the prescribing doctors' phone numbers and the pharmacy contact number, potential side effects to be cautious of with respect to the prescribed medications, etc. The additional compliance or prescription information could be provided on either side of the compliance sheet 50 as desired, but is preferably disposed on the first side 51 having compliance calendar 52 as to not distract away from the value of the advertising information 72 on the second side 71 of sheet 50. However, the additional information must be presented in a manner that does not affect the effectiveness of compliance calendar 52. As such, the embodiment exemplified in FIG. 4 providing only one frequency reminder is particularly useful in saving sufficient for additional information when such additional information is desired. On the other hand, the embodiment of calendar 52 exemplified in FIG. 4 having multiple frequency reminders should include very little, if any, additional information so that compliance calendar 52 may be sufficiently sized for accurate and reading.

In preferred embodiments, compliance sheets 50 are distributed to patients with their prescribed medications by the pharmacy. As noted above, in most preferred embodiments, the compliance sheet 50 is distributed to the patient when filling all of the patient's monthly prescriptions as part of a medication synchronization program. However, as noted above, a third party could also compile dosage information from any number of prescriptions for the patient and provide compliance sheets 50 to be used with pill tray 10. The patient then secures the compliance sheet 50 to the cover 20 of an appropriate tray 10 having daily sections 30 corresponding to the one or more frequency reminders of calendar 52 of compliance sheet 50. In alternate embodiments, the compliance calendar 52 may be used by the patient in dosing the pill tray 10 without having to be secured to the cover 20. In other words, the calendar 52 as described above may, for example, be suitable for hanging as by magnet or adhesive on a refrigerator or medicine cabinet. The patient may then refer to the compliance calendar 52 when dosing the pill tray 10 and when keeping track of compliance as described above. In such an embodiment, the pill tray may or may not include the cover 20.

In another aspect of the disclosure, the compliance sheets 50 may be transmitted via a pharmacy computer system to a customer computer system. For example, an appropriate compliance sheet 50 having compliance calendar 52 may be emailed to the customer upon filling of a prescription and then printed off by the customer for securing to the cover 20 of pill tray 10. Alternatively, an electronic version of compliance sheet 50 having compliance calendar 52 with dosing instructions may be transmitted to the customer through a software application downloaded to the customer's computer system or accessed through a standard Internet browser.

When the compliance sheet 50 is provided through a software application, the customer preferably references the calendar 52 in dosing the pill tray 10. Further, the calendar 52 and related application are preferably interactive such that the customer can keep track of their compliance directly from their computer, tablet, and/or smartphone devices through the application. Additional interactive features could include the ability to click on certain prescribed medications for more information, such as warning information or pictorial representations of the pharmaceuticals, click on a sequence section 58 of calendar 52 to see expanded details regarding prescribed medications for that particular dosing sequence, click on a pharmacy link to order refills or submit questions to the pharmacy, etc. Further, particularly when the software application is downloaded to a customer's smartphone or tablet device, the application may provide automatic reminders to the customer when certain medications should be taken. The customer may also interact with the application by responding as to whether it took the medication and at what time the medication was taken, and the application automatically keeps track of the customer's compliance based on the customer's responses. The customer can then save each compliance calendar for future reference by the customer or, with permission, appropriate medical personnel. Compliance information may also be automatically transmitted to the pharmacy or medical personnel for continual monitoring. For example, if the patient has not taken a prescribed sequence of medications at the appropriate time, the pharmacy computer system may automatically call the patient or send another reminder through the software application. Relatedly, the pharmacy may also communicate replacement compliance sheets 50 and/or additional information to the customer such as prescription changes, warnings, refill notifications, promotional information, etc. through the application.

Figure 9:
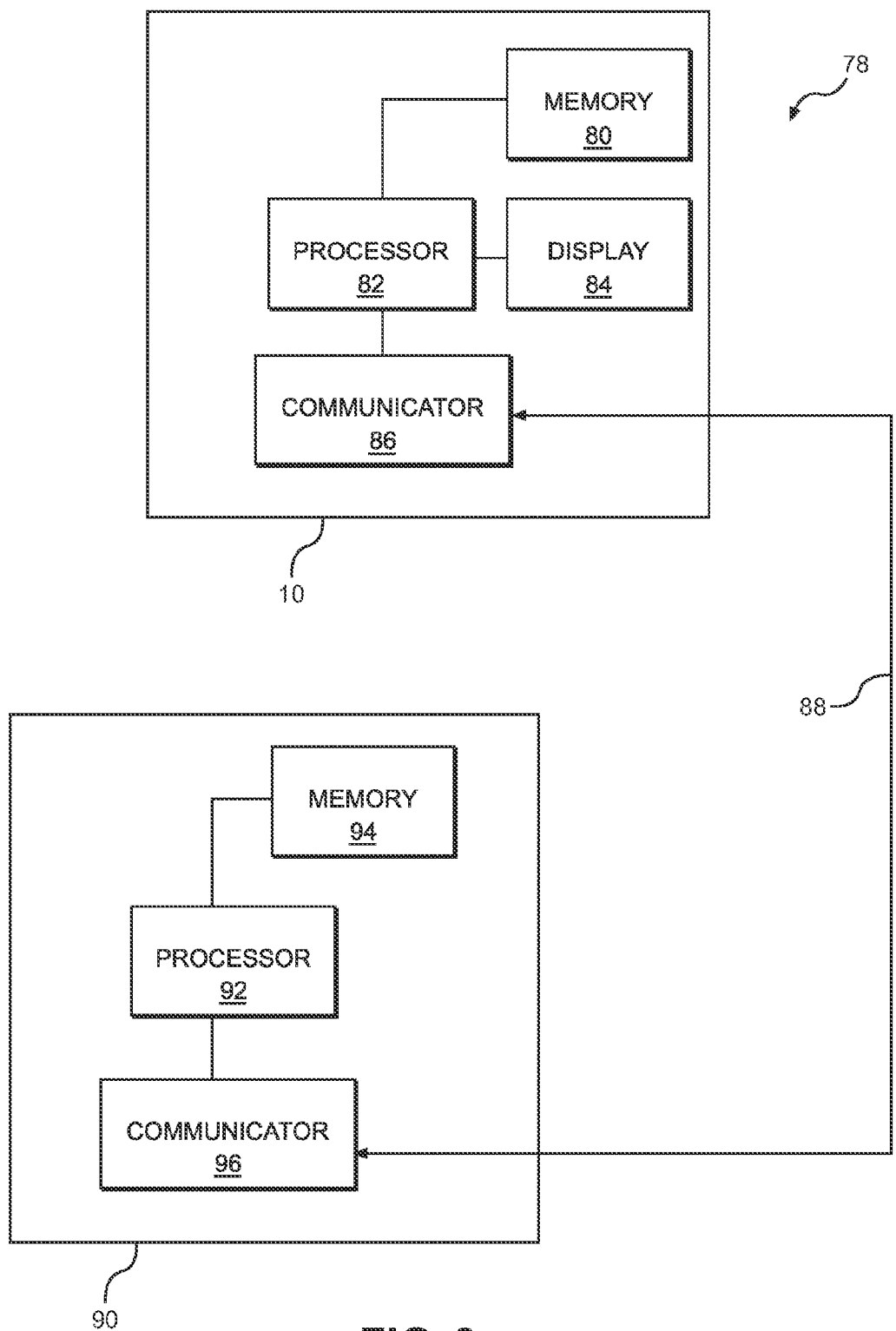
FIG. 9 depicts a schematic diagram of a pill tray having an electronic display in communication with a pharmacy computer system according to one embodiment of the disclosure.

According to embodiments in which an electronic version of compliance sheet 50 is transmitted to the patient through a software application, the cover 20 of pill tray 10 is preferably in a form similar to an inexpensive smartphone or otherwise stripped down smartphone or tablet-computing device. Alternatively, a user's existing tablet or smartphone is operable to secure to the base portion 12 of pill tray 10 to form an electronic display for the software application. Referring to the schematic diagram of FIG. 9, a system 78 allowing the pharmacy to communicate with the pill tray 10 is shown. The pill tray 10, with all components preferably provided in the cover 20, includes a memory 80 connected to a processor 82. The application is stored to the memory 80 and the processor 82 is operable to be in communication with an electronic display 84 for displaying a user interface of the software application to the user. In preferred embodiments, the electronic display 84 is in the form of a touch screen in order for the user to easily interact with the software application. A communicator 86 is connected to the processor 82 and is operable to connect to communication network 88. In preferred embodiments, the communicator 86 of the pill tray 10 is operable to wirelessly connect to the communication network 88 such as through a cellular or wireless Internet connection. As shown, the pharmacy computer system 90 also includes a processor 92, memory 94, and communicator 96 operable to connect to communication network 88. Thus, communicator 86 of cover 20 is operable to wirelessly transmit and receive information and programming instructions from the communicator 96 of the pharmacy computer system 90 through communication network 88. In alternate embodiments, or in addition to the wireless connection, communicator 86 is operable to transmit and receive information from the pharmacy computer system 90 through a transfer device such as a USB storage device.

In another aspect of the disclosure, the base portion 12 of pill tray 10 may include limited and inexpensive electrical components specifically directed to improve compliance. For example, each sequence compartment 32 could include lights to illuminate an appropriate compartment 32 when it is time to take the medications dosed to that compartment. This helps ensure the patient takes the medication from the correct compartment 32. Additionally, the appropriate sequence section 58 of calendar 52 may be highlighted on the electronic display indicating which sequence of medications should be taken. Sensors could also be connected to the daily sections 30 and/or each sequence compartment 32 to alert the user when the particular section or compartment has not been dosed correctly. For example, weight sensors could measure the weight of a daily section and compare to a proper weight range for the daily section based on the intended dosages and alert the patient when the actual weight does not fall within the appropriate weight range. Further, alerts could be provided when the daily sections 30 are not properly secured to the base portion 12.

Accordingly, the disclosure provides a pill tray and associated calendar that permit patients in a simple and cost-effective manner to accurately and intuitively dose the pill tray, to be continually reminded as to how to take prescribed medications, and to maintain a record of the patient's compliance.

The foregoing description of preferred embodiments for this disclosure have been presented for purposes of illustration and description. They are not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A prescription compliance system for improving patient compliance in taking a plurality of prescribed medications each having prescription instructions instructing a user to take the prescribed medication at prescribed times, the prescription compliance system comprising:
    a pill tray including a base portion having a pill tray layout including a plurality of frequency sections and a plurality of sequence compartments within each frequency section; and
    a compliance calendar physically separable from the pill tray having a calendar layout including a plurality of frequency reminders and a plurality of sequence reminders within each frequency reminder to provide a plurality of demarcated sequence sections, each of the plurality of demarcated sequence sections corresponding to one of the plurality of sequence compartments of the pill tray and having dosing instructions specific to the user including identification of the plurality of prescribed medications that should be dosed to the corresponding sequence compartment of the pill tray according to the prescription instructions of the plurality of prescribed medications to provide graphical dosage instruction information for the user in dosing each of the sequence compartments of the pill tray.

2. The prescription compliance system of claim 1 wherein the pill tray is a weekly pill tray such that each of the plurality of frequency sections corresponds to a particular day of the week and each of the plurality of sequence compartments of each frequency section corresponds to a particular time of day to take the prescribed medication during the particular day of the week.

3. The prescription compliance system of claim 1 wherein each of the plurality of frequency sections is operable to be removed from the base portion independently of other frequency sections.

4. The prescription compliance system of claim 1 wherein the positioning of the demarcated sequence sections of the calendar layout mimics positioning of the sequence compartments in the pill tray layout.

5. The prescription compliance system of claim 1 wherein the pill tray includes a cover operable to move between an open position and a closed position, the compliance calendar being dimensioned and configured to be secured to the cover of the pill tray such that the compliance calendar is visible to a user when the cover is in the open position.

6. The prescription compliance system of claim 5 further comprising an advertisement secured to the cover of the pill tray such that the advertisement is visible to the user when the cover is in the closed position.

7. The prescription compliance system of claim 6 wherein the cover is composed of a clear plastic and the compliance calendar is printed on a first side of a sheet material and the advertisement is printed on a second side of the sheet material, the sheet material being configured to be secured to the cover such that the first side is visible to the user when the cover is in the open position and the second side is visible to the user when the cover is in the closed position.

8. The prescription compliance system of claim 1 wherein the compliance calendar is provided to the user at the pharmacy as a sheet material.

9. The prescription compliance system of claim 1 wherein the compliance calendar is provided to the user in electronic format.

10. The prescription compliance system of claim 1 wherein the pill tray includes an electronic display for displaying the compliance calendar to the user.

11. The prescription compliance system of claim 10 wherein the pill tray is in communication with a pharmacy computer system for receiving the compliance calendar in an electronic format to be displayed on the electronic display.

12. A prescription compliance system for improving patient compliance in taking a plurality of prescribed medications each having prescription instructions providing that the prescribed medication is to be taken according to a particular sequence schedule each day, the prescription compliance system comprising:
- a pill tray including a base portion having a plurality of daily sections and a plurality of sequence compartments within each daily section, the plurality of sequence compartments configured for receiving the plurality of prescribed medications according to the sequence schedule of each of the plurality of prescribed medications, and
- a compliance calendar physically separable from the pill tray including only one daily reminder having a plurality of sequence reminders to provide a plurality of demarcated sequence sections each corresponding to one of the plurality of sequence compartments within each daily section of the pill tray, each of the plurality of demarcated sequence sections having dosing instructions specific to a patient including identification of the plurality of prescribed medications that should be dosed to the corresponding sequence compartments of the pill tray according to the prescription instructions of the plurality of prescribed medications to provide graphical dosage instruction information for the patient in dosing each of the sequence compartments of the pill tray.

13. The prescription compliance system of claim 12 wherein the compliance calendar is provided to the user as a sheet material, the sheet material further comprising a second compliance calendar including at least a plurality of daily reminders corresponding to a prescription period for recording when the user complied with the prescription instructions.

14. The prescription compliance system of claim 13 wherein the second compliance calendar is operable to be removed from the sheet material for record keeping of compliance.

15. The prescription compliance system of claim 14 wherein both compliance calendars are operable to be removed from the sheet material together for record keeping of compliance.

16. The prescription compliance system of claim 12 wherein the pill tray further includes a cover operable to move between an open position and a closed position, the cover for covering the plurality of frequency sections in the closed position.

17. The prescription compliance system of claim 16 wherein the compliance calendar and the cover of the pill tray are dimensioned and configured to removeably secure the compliance calendar to the cover of the pill tray such that the compliance calendar is visible to a user when the cover is in the open position.

18. The prescription compliance system of claim 17 further comprising an advertisement secured to the cover of the pill tray such that the advertisement is visible to the user when the cover is in the closed position.

19. The prescription compliance system of claim 18 wherein the compliance calendar is printed on a first side of a sheet material and the advertisement is printed on a second side of the sheet material, and wherein the cover is composed of a clear plastic and the sheet material is secured to the cover such that the first side is visible to the user when the cover is in the open position and the second side is visible to the user when the cover is in the closed position.

20. The prescription compliance system of claim 12 wherein each daily section is secured to the base portion in a pill tray layout and the compliance calendar provides the demarcated sequence sections in a calendar layout that mimics positioning of the sequence compartments in the pill tray layout.

21. The prescription compliance system of claim 12 wherein each of the plurality of frequency sections is operable to be removed from the base portion independently of other frequency sections.

22. The prescription compliance system of claim 12 wherein the compliance calendar is provided to the user in electronic format.

23. The prescription compliance system of claim 12 wherein the pill tray includes an electronic display for displaying the compliance calendar to the user.

24. The prescription compliance system of claim 12 wherein the pill tray is in communication with a pharmacy computer system for receiving the compliance calendar in an electronic format to be displayed on the electronic display.

25. A method for improving patient compliance in taking a plurality of prescribed medications each having prescription instructions providing that the prescribed medication is to be taken each day according to a sequence schedule, the method comprising:
- providing a pill tray to a patient including a base portion having a plurality of daily sections and a plurality of sequence compartments within each daily section, the plurality of sequence compartments configured for receiving the plurality of prescribed medications according to the sequence schedule of each of the plurality of prescribed medications;
- dispensing each of the plurality of prescribed medications to the patient;
- providing a compliance calendar to the patient, the compliance calendar physically separable from the pill tray and including at least one frequency reminder having a plurality of demarcated sequence sections corresponding to the plurality of sequence compartments within each daily section, each of the plurality of demarcated sequence sections including dosing instructions specific to the patient including identification of the plurality of prescribed medications that should be dosed to the corresponding sequence compartments of the pill tray according to the prescription instructions of the plurality of prescribed medications to provide graphical dosage instruction information for the patient in dosing each of the sequence compartments of the pill tray; and
- upon changes to the prescription instructions of the plurality of prescribed medications, providing a replacement compliance calendar to the patient to provide graphical dosage instruction information for the patient in dosing each of the sequence compartments of the pill tray according to the changed prescription instructions.

26. The method for improving patient compliance of claim 25 wherein the pill tray includes a cover composed of a clear material operable to move between an open position and a closed position and wherein the compliance calendar is provided on a first side of a compliance sheet and an advertisement is provided on a second side of the compliance sheet, the compliance sheet being dimensioned and configured to be removeably secured to the cover of the pill tray such that the compliance calendar is visible to the patient when the cover is in the open position and the advertisement is visible to the user when the cover is in the closed position.

27. The method for improving patient compliance of claim 26 wherein the step of providing the pill tray to the patient includes a pharmacy providing the pill tray to the patient at a reduced cost by selling advertising space on the second side of the compliance sheet to third parties.

28. The method for improving patient compliance of claim 25 wherein the compliance calendar is disposed on a compliance sheet and the method further comprises instructing the patient to record compliance in taking the plurality of prescribed medications directly on the compliance sheet.

29. The method for improving patient compliance of claim 28 wherein the compliance calendar includes only one frequency reminder and the compliance sheet further includes a second compliance calendar having at least a plurality of frequency reminders with no dosing instructions for recording compliance in taking the plurality of prescribed medications directly on the compliance sheet.

30. The method for improving patient compliance of claim 29 wherein the second compliance calendar is operable to be removed from the compliance sheet.

31. The method for improving patient compliance of claim 25 wherein the step of providing the compliance calendar and the replacement compliance calendar to the patient includes transmitting the compliance calendar and, upon changes to the prescription instructions of the plurality of prescribed medications, the replacement compliance calendar from a pharmacy computer system to a customer computer system.

32. The method for improving patient compliance of claim 31 wherein the customer computer system includes an electronic display operable to be secured to the pill tray for displaying the compliance calendar and, upon changes to the prescription instructions of the plurality of prescribed medications, the replacement compliance calendar to the patient.

33. The method for improving patient compliance of claim 31 wherein the customer computer system includes an electronic display having a touch screen for displaying the compliance calendar to the patient and the compliance calendar is interactive for recording compliance in taking the plurality of prescribed medications directly on the electronic display.

34. The method for improving patient compliance of claim 33 further comprising transmitting the recorded compliance from the customer computer system to the pharmacy computer system.

* * * * *